(12) United States Patent
Otsubo et al.

(10) Patent No.: US 7,503,912 B2
(45) Date of Patent: Mar. 17, 2009

(54) DISPOSABLE WEARING ARTICLE

(75) Inventors: Toshifumi Otsubo, Kagawa-ken (JP); Tomoko Sugito, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 10/920,299

(22) Filed: Aug. 18, 2004

(65) Prior Publication Data

US 2005/0043698 A1 Feb. 24, 2005

(30) Foreign Application Priority Data

Aug. 19, 2003 (JP) .............................. 2003-207943
Aug. 4, 2004 (JP) .............................. 2004-227611

(51) Int. Cl.
*A61F 13/15* (2006.01)
(52) U.S. Cl. ................... 604/387; 604/367; 604/385.01
(58) Field of Classification Search ............ 604/385.27, 604/386–391, 367
See application file for complete search history.

(56) References Cited

U.S. PATENT DOCUMENTS 6,213,991 B1 * 4/2001 Kling et al. ............ 604/385.01
2005/0177126 A1 * 8/2005 Kurata ........................ 604/387

FOREIGN PATENT DOCUMENTS

WO WO 01/87209 A1 11/2001

* cited by examiner

*Primary Examiner*—Michele Kidwell
(74) *Attorney, Agent, or Firm*—Lowe Hauptman Ham & Berner, LLP (57) ABSTRACT

A disposable wearing article includes elastic members interposed between inner and outer sheets and attached in a stretched state to these inner and outer sheets. A base sheet constituting a component of a hook part of a mechanical fastener is oriented to extend across the elastic members and attached to the outer sheet. Of the outer sheet, a region in which the outer sheet is attached to the base sheet and peripheral regions having dimensions m, n as measured from side edges of the base sheet in a width direction of the article are attached neither to the elastic members nor to the inner sheet. The outer sheet is attached to the inner sheet in regions defined outside those peripheral regions.

14 Claims, 10 Drawing Sheets

DISPOSABLE WEARING ARTICLE

RELATED APPLICATIONS

The present application is based on, and claims priority from, Japanese Application Serial Number 2003-207943, filed Aug. 19, 2003, and Japanese Application Serial Number 2004-227611, filed Aug. 4, 2004, the disclosures of which are hereby incorporated by reference herein in their entirety.

BACKGROUND OF THE INVENTION

The present invention relates to a disposable wearing article such as, for example, a disposable diaper, a training pant, a diaper for incontinent patient, a pant to fold urine-absorbent pad and a diaper pad.

WO 01/87209 A1 (hereinafter referred to as "Citation") discloses a process for making absorbent garment. A training pant obtained using this process comprises a body fluid absorbent chassis and a fastening system. The chassis is provided in front and rear waist regions with elastic members stretchably extending in a waist surrounding direction. A hook part and a loop part of a mechanical fastener constituting the fastening system are attached to the chassis so that these hook and loop parts extend across the elastic members.

In the training pant disclosed in Citation, the chassis is formed with gathers as the elastic members contract and thereupon the hook part as well as the loop part both attached to the chassis also may be formed with gathers. The hook part most commonly used has a relatively high stiffness and, if such hook part is used in the training pant, the hook part will be substantially free from such formation of gathers. However, in the case of the training pant using the hook part having a lower stiffness, i.e., more soft and flexible hook part, the hook part is also apt to be formed with gathers. If the hook part is formed with gathers, some of many hooks formed on the hook part will be laid low in troughs of these gathers and unable to come in engagement with the loop part. The number of effective hooks is thus decreased and the hook part will be easily disengaged from the loop part. Compared to the hook part which is flat and the loop part engaged with such hook part, the hook part formed with gathers and the loop part engaged with such hook part are readily disengaged from each other as these two parts are pulled in opposite directions, because a so-called peeling force is easily generated between these two parts. As will be apparently understood from the foregoing description, the formation of gathers on the hook part is undesirable for the disposable wearing article, and the formation of gathers on the loop part is also undesirable. In the same case the mechanical fastener can be replaced with a fastener comprising a sticky sheet coated with an adhesive agent and a sheet constituting a target zone for the sticky sheet. And gathers on the sticky sheet and the target sheet are also undesirable.

SUMMARY OF THE INVENTION

It is an object of the present invention to improve the wearing article provided with such a fastener as a mechanical fastener so that at least a part of the fastener is ford with none of gathers even when the elastic members of the wearing article contract.

The present invention is directed to a disposable wearing article, which comprises:

a crotch region having a back-and-forth direction and a width direction orthogonal to each other;

a first waist region and a second waist region extending forward and rearward from the crotch region in the back-and-forth direction of the crotch region, the first and second waist regions respectively having end portions each extending in the width direction;

at least in the first waist region of the first waist region and the second waist region, a plurality of elastic members stretched in the width direction being interposed between a first sheet and a second sheet placed upon each other;

and the first sheet being formed with a first fastening means constituting a fastener comprising the first fastening means and a second fastening means destined to be engaged with each other while the second waist region being formed with the second fastening means.

The article according to the present invention further comprises: the plurality of elastic members comprising at least a single first elastic ember having a high stretch stress and a plurality of second elastic members having a stretch stress lower than that of the first elastic member and located aside from the first elastic member toward the crotch region; and the first fastening means comprising a base sheet and a plurality of first fastening elements formed on one surface of the base sheet and extends across the plurality of second elastic members in the back-and-forth direction, a surface of the base sheet opposed to the one surface being attached to a sheet member locating in the first waist region and having a size larger than the base sheet and a stiffness lower than the base sheet, regions of the sheet member lying on both sides of the base sheet and spaced from respective side edges of the base sheet by a given dimension being attached to one of said first and the second sheets while a region defined between the two regions being attached neither to the first sheet nor to the second sheet and the second elastic members.

The article according to the present invention may include preferred embodiments as follows:

The sheet member is formed from the first sheet and regions of the first sheet spaced from side edges of the base sheet in the width direction by a given dimension are attached to the second sheet and the second elastic members.

The first sheet defines one of an outer sheet of the wearing article facing a garment and an inner sheet of the wearing article facing the wearer's skin.

The sheet member is formed from a third sheet provided separately of the first sheet and the second sheet and extends outward beyond the side edges of the base sheet on both sides thereof so that the third sheet may be attached to the first sheet in its regions spaced from the side edges of the base sheet by a given dimension in the width direction while a region defined between the regions spaced from the side edges of the base sheet is not attached to the first sheet.

The first fastening means is one of a hook part and a loop part constituting a mechanical fastener and the second fastening means is the rest of the mechanical fastener, the first fastening elements being ones of hooks of the hook part and loops of the loop part.

The first fastening means is either a sticky sheet coated with an adhesive agent or a sheet constituting a target zone for the sticky sheet to be attached repeatedly while the second fastening means is the rest of the sticky sheet and the sheet constituting the target zone, the first fastening elements being one of the adhesive agent and the surface of the sheet constituting the target zone.

DETAILED DESCRIPTION OF THE PREFERRED EMBODIMENTS

Details of the disposable wearing article according to the present invention will be more fully understood from the description of a disposable diaper as a typical embodiment of the invention given hereunder with reference to the accompanying drawings.

Figure 1:
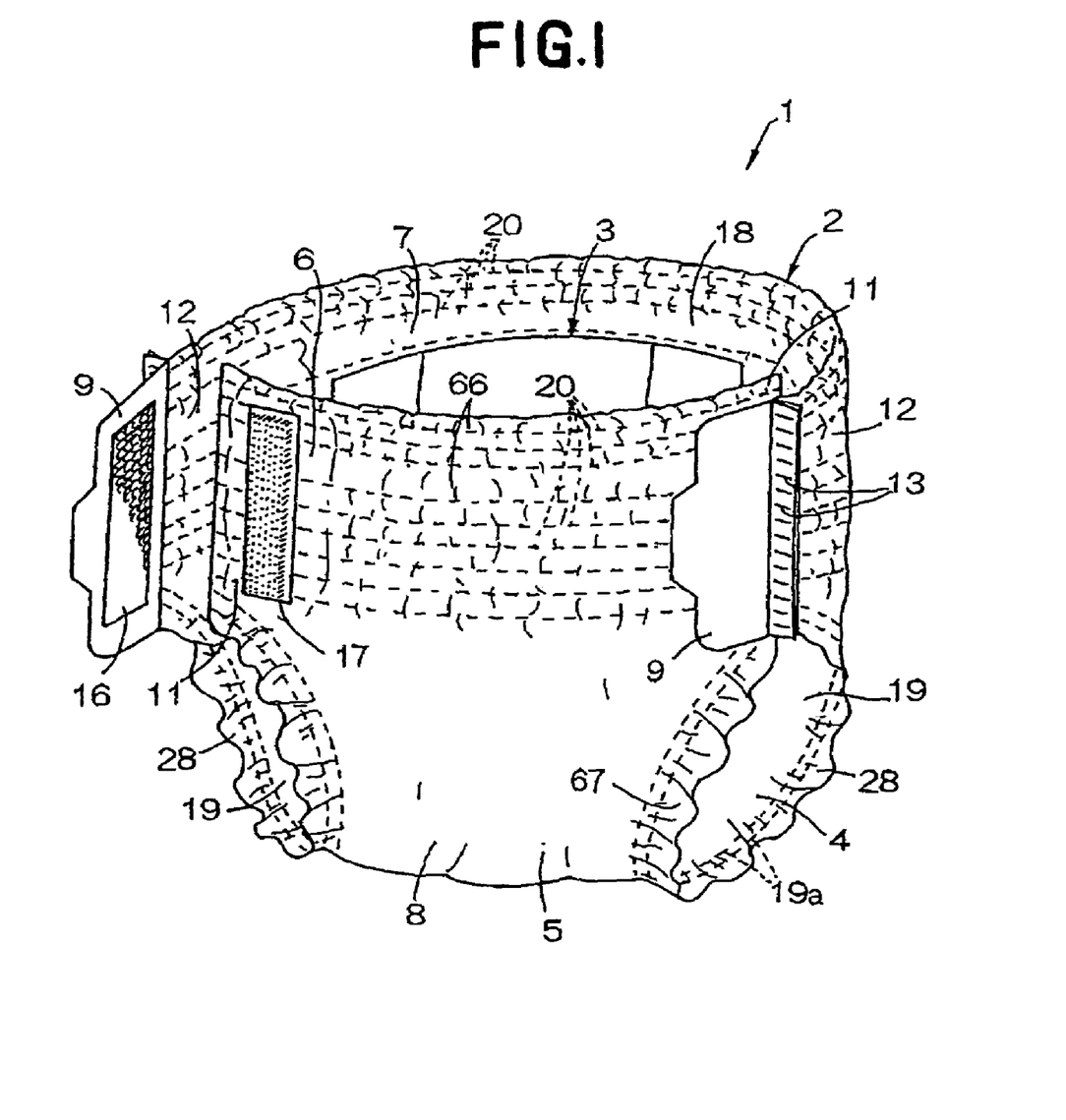
FIG. 1 is a perspective view showing a disposable diaper as a typical embodiment of the invention.

FIG. 1 is a perspective view showing a disposable diaper 1 basically comprising a body cover 2 and a body fluid absorbent panel 3. The body cover 2 defines a crotch region 8, a front waist region 6 extending forward from the crotch region 8 and a rear waist region 7 extending reward from the crotch region 8. The regions 6, 7, 8 are formed from a first sheet facing the wearer's garment (not shown), i.e., an outer sheet 5 and a second sheet facing the wearer's skin (not shown), i.e., an inner sheet 4. A pair of flaps 9 formed from a third sheet provided separately of the inner and outer sheets 4, 5 are attached by means of bonding or welding to transversely opposite side edge portions 12 of the rear waist region 7 at spots 13 arranged intermittently in a vertical direction as viewed in FIG. 1. Since the side edge portion 12 and the flap 9 is attached to each other in flat, the flap 9 has a tendency to overlap by itself with the outer sheet 5 in the front waist region 6. Each of the flaps 9 is provided on inner surface thereof with a loop part 16 constituting a part of a mechanical fastener well known, for example, by the trademark "Velcro" or "Magic Tape". To cooperate with the loop part 16, the front waist region 6 is provided on its outer surface of each side edge portion 11 with a hook part 17 constituting a part of the mechanical fastener. The hook part 17 is attached by means of bonding or welding to the outer surface of each side edge portion 11. By pressing the loop part 16 and hook part 17, both of which constitute a fastening means of the diaper 1, against each other, the front and rear waist regions 6, 7 are detachably connected with each other along the mutually facing side edge portions 11, 12 through the flap 9. FIG. 1 illustrates the diaper 1 in the state wherein one of the side edge portions 11 has been connected with one of the side edge portions 12 and the other of the side edge portions 11 is not connected with the other of the side edge portions 12. Upon connection of both of the side edge portions 11 with both of the side edge portions 12, the diaper 1 is formed with a waist-hole 18 and a pair of leg-holes 19. The diaper 1 formed in this manner further includes waist-surrounding elastic members 20 extending along the waist-hole 18 and leg-surrounding elastic members 19a respectively extending along the leg-holes 19. The body cover 2 is formed with gathers 66, 67 undulating in the waist surrounding direction and in the leg surrounding direction, respectively, as those elastic members 20, 19a contract.

Figure 2:
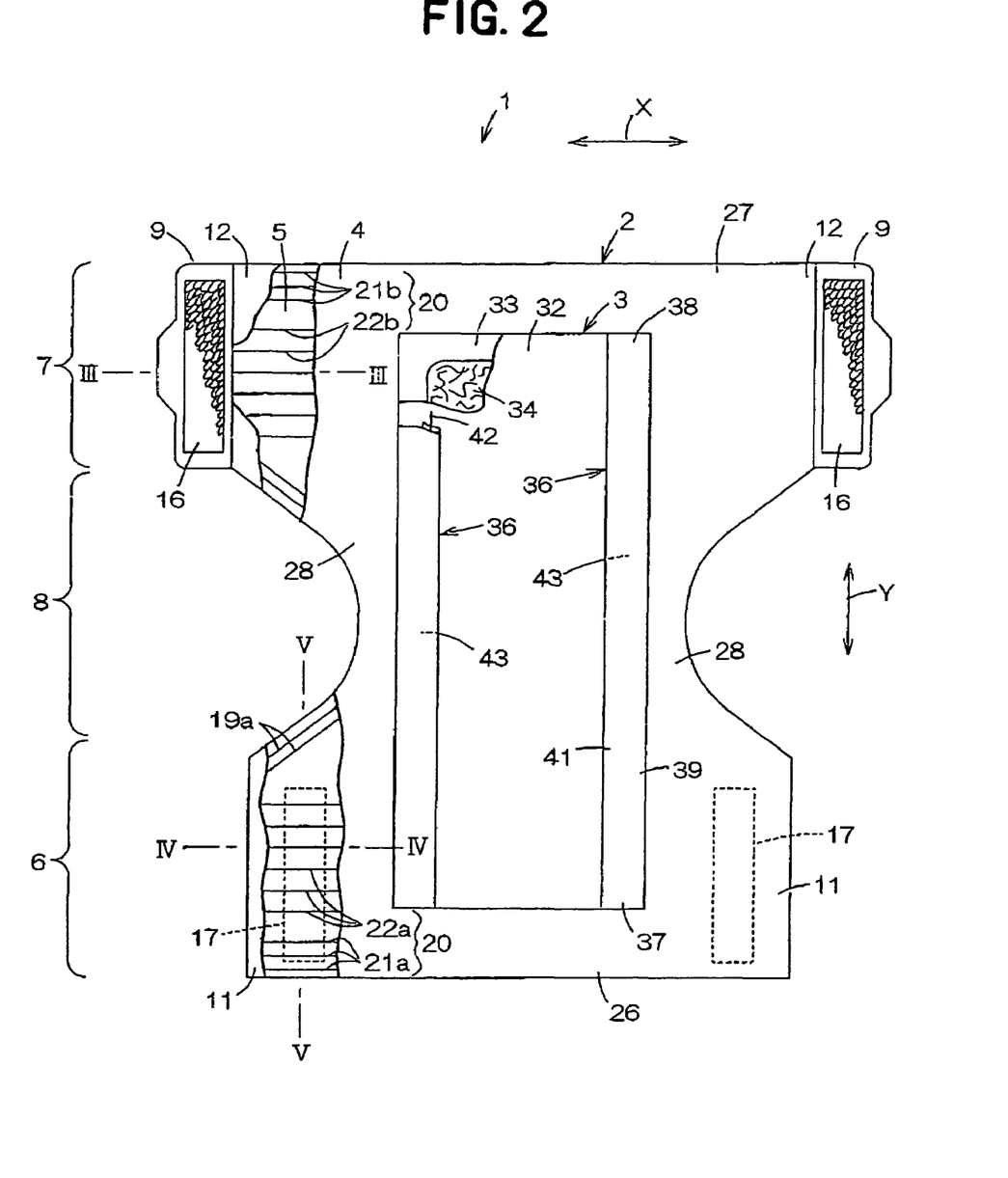
FIG. 2 is a partially cutaway plan view, showing the developed disposable diaper.

FIG. 2 is a partially cutaway plan view showing the diaper 1. FIG. 2 illustrates the diaper 1 developed by disconnecting the side edge portions 11 of the front waist region 6 from the flaps 9 provided on the side edge portions 12 of rear waist region 7. The diaper 1 has a width direction indicated by a double-headed arrow X and a back-and-forth direction orthogonal to the width direction indicated by/a double-headed arrow Y. The width direction X corresponds to the waist surrounding direction. Of the body cover 2, the front region 6 has a dimension measured between its side edge portions 11, 11 having generally the same dimension as that of the rear region 7 measured between its side edge portions 12, 12. The front and rear waist regions 6, 7 respectively have a front end portion 26 and a rear end portion 27 both extending in the width direction. Transversely opposite side edge portions 28 of the crotch region 8 curve inward to describe circular arcs which are convex inward. The waist-surrounding elastic members 20 provided on the body cover 2 comprise at least a single first elastic member 21a for the front waist region 6 attached in a stretched state to the front end portion 26 so as to extend between the side edge portions 11, 11; at least a single first elastic member 21b for the rear waist region 7 attached in a stretched state to the rear end portion 27 so as to extend between the side edge portions 12, 12; a plurality of second elastic members 22a for the front waist region 6 attached in a stretched state to a zone of the front waist region 6 defined between the first elastic member 21a (See FIG. 1) and the side edge portion 28 of the crotch region 8 so as to extend between the side edge portions 11, 11; and a plurality of second elastic members 22b for the rear waist region 7 attached in a stretched state to a zone of the rear waist region 7 defined between the first elastic member 21b and the side edge portion 28 of the crotch region 8 so as to extend between the side edge portions 12, 12. The respective first elastic members 21a, 21b have a stretch (or tensile) stress higher than that of the respective second elastic members 22a, 22b so that these first elastic members 21a, 21b may be pressed against the wearer's waist more tightly than the respective second elastic members 22a, 22b. The body cover 2 further includes the leg-surrounding elastic members 19a attached in a stretched state to the side edge portions 28 of the crotch region 8. The waist-surrounding elastic members 20 and leg-surrounding elastic members 19a are interposed between the inner sheet 4 and the outer sheet 5 and bonded to the sheets 4, 5 except the vicinity of the hook part 17 as will be described in detail with reference to FIGS. 5 and 6. Preferably, the elastic members 20, 19a are intermittently bonded to those sheets 4, 5.

As depicted in FIG. 2, the body fluid absorbent panel 3 comprises a liquid-pervious upper sheet 32, a liquid-impervious lower sheet 33 and a body fluid absorbent core 34 interposed between these two sheets 32, 33. The upper and lower sheets 32, 33 extend outward beyond a surrounding edge of the core 34 and the extensions of these sheets 32, 33 are overlapped and adhesively bonded or welded together. Transversely opposite side edge portions of such body fluid absorbent panel 3 are provided with leak-barrier cuffs 36 preferably formed from liquid-impervious sheet. Each of the leak-barrier cuffs 36 is attached to the upper sheet 32 at its front and rear end portions 37, 38 and along its outer side edge portion 39 but not attached to the upper sheet 32 along its inner side edge portion 41. An elastic member 42 extending in the back-and-forth direction Y is bonded in a stretched state to the inner side edge portion 41. The leak-barrier cuffs 36 formed in this manner respectively define pockets 43 adapted to receive body fluids flowing in the width direction X. The body fluid absorbent panel 3 has its lower sheet 33 bonded to the inner sheet 4 of the body cover 2 by means of hot melt adhesive (not shown).

Figure 3:
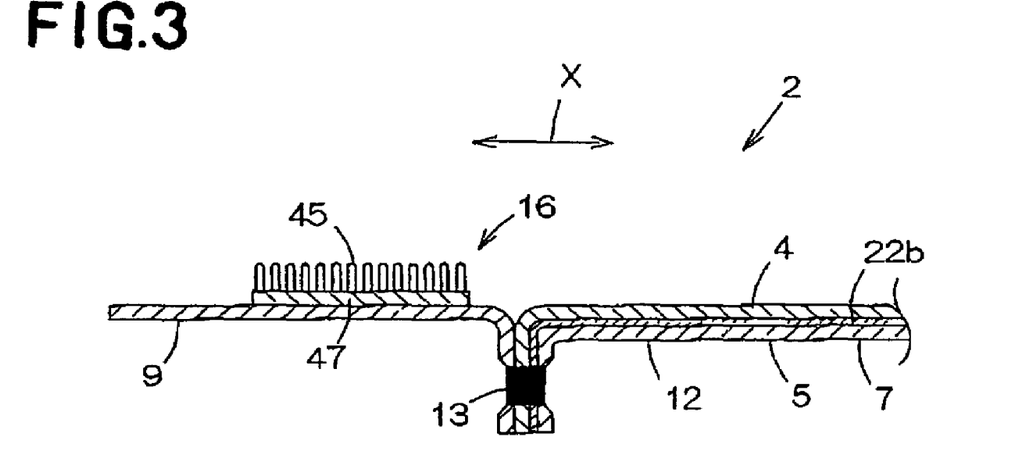
FIG. 3 is a sectional view taken along the line III-III in FIG. 2.

FIG. 3 is a sectional view taken along the line III-III in FIG. 2. In the body cover 2, the side edge portions 12 of the rear waist region 7 are overlapped and attached to the respective flaps 9 at the spots 13. In each of the side edge portions 12, the first and second elastic members 21b, 22b for the rear waist region 7 are interposed between the inner and outer sheets 4, 5 and intermittently bonded to the sheets 4, 5. These elastic members 21b, 22b extend to the spots 13. It should be understood here that the first elastic members 21b can not be seen in FIG. 3. The flap 9 is attached to the associated side edge portion 12 so that the flap 9 is not peeled off from the side edge portion 12 even when the flap 9 is pulled in the width direction X. A base sheet 47 constituting a loop part 16 is attached to the inner surface of the flap 9 and the loop part 16 has a plurality of loops 45 formed on the base sheet 47.

Figure 4:
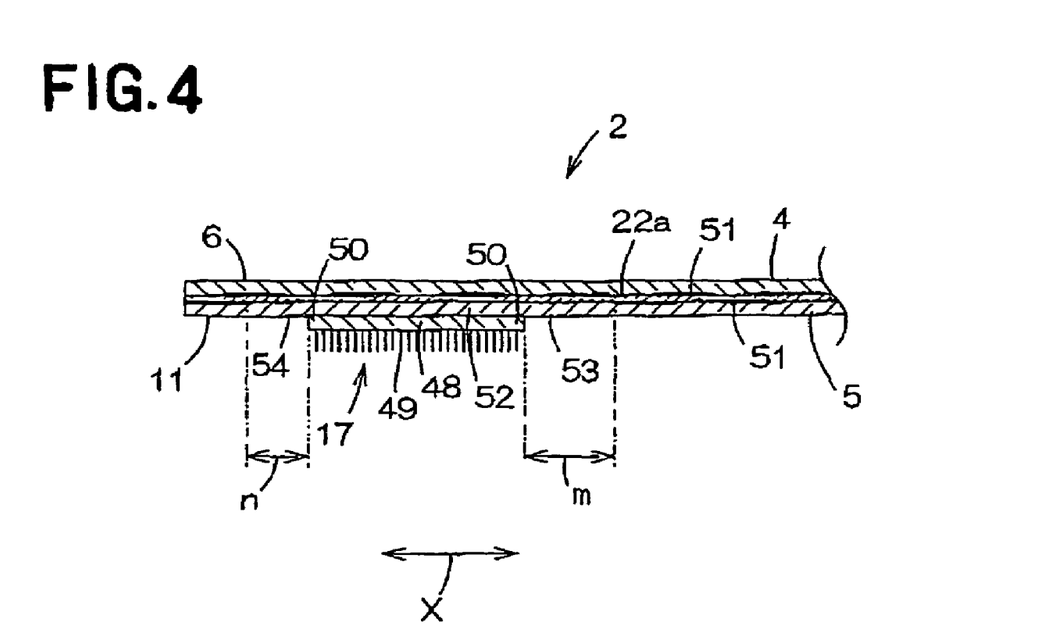
FIG. 4 is a sectional view taken along the line IV-IV in FIG. 2.
Figure 5:
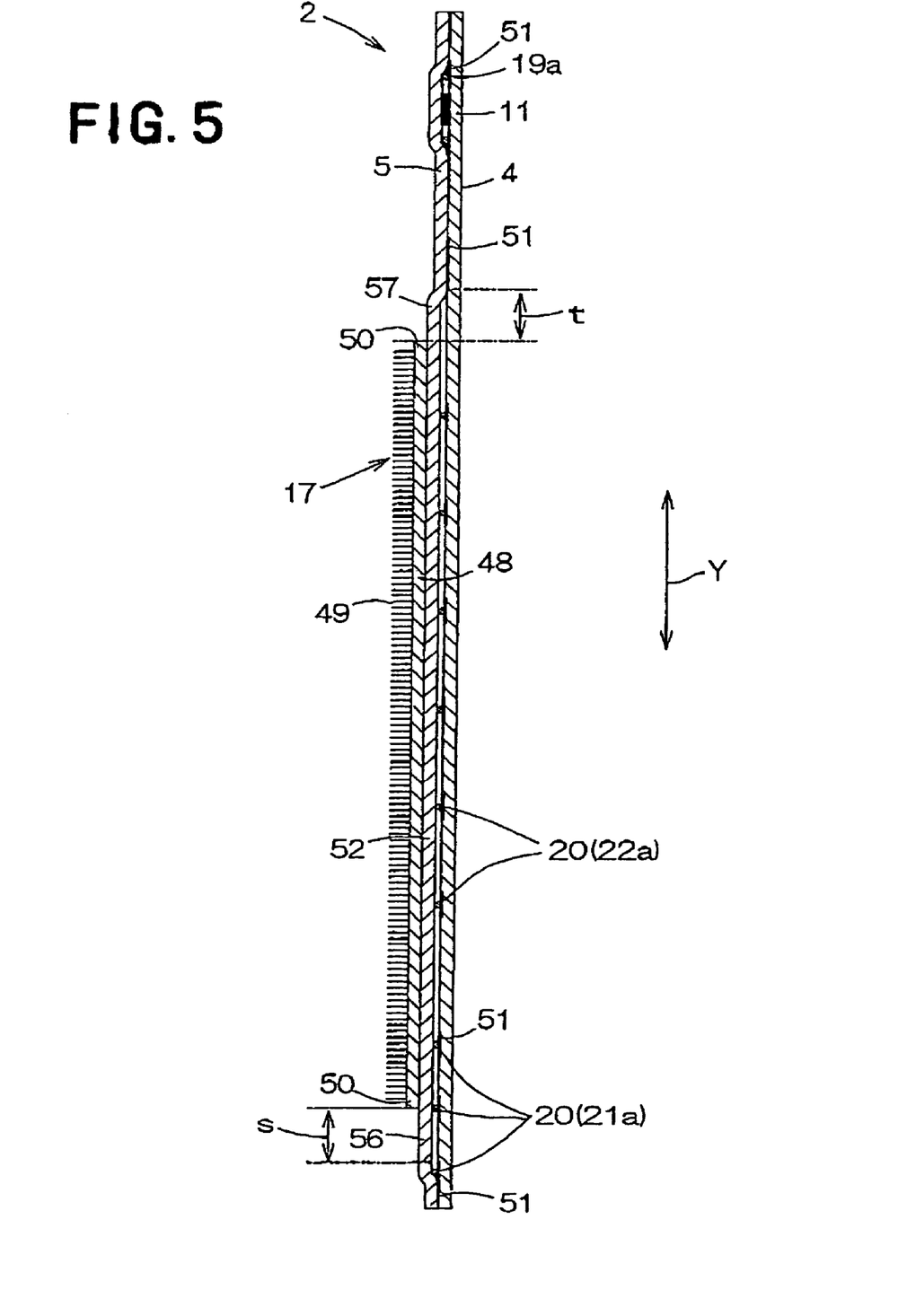
FIG. 5 is a sectional view taken along the line V-V in FIG. 2.

FIGS. 4 and 5 are sectional views taken along lines IV-IV and V-V, respectively, in FIG. 2. In the body cover 2, the side edge portions 11 of the front waist region 6 are provided with the hook parts 17 each comprising a base sheet 48 attached to the outer surface of the outer sheet 5 and a plurality of hooks 49 rising from this base sheet 48 as fastening elements. Referring to FIG. 4, the inner sheet 4 of the body cover 2, the outer sheet 5 and the second elastic members 22a are bonded together by means of a hot melt adhesive 51 intermittently in a longitudinal direction of the second elastic members 22. It should be minded here that a region 52 of the outer sheet 5 placed on and bonded to the base sheet 48 and regions 53, 54 of the outer sheet 5 lying on both sides of the base sheet 48 in the width direction X and having width dimensions m and n measured from the respective side edges 50 of the base sheet 48 are bonded neither to the inner sheet 4 nor to the second elastic members 22a. The dimensions m and n are preferably in a range of 2 to 20 mm. Referring to FIG. 5, a region 52 of the outer sheet 5 placed on the base sheet 48 of the hook part 17 and regions 56, 57 of the outer sheet 5 lying on both sides of the base sheet 48 in the back-and-forth direction and having width dimensions s and t measured from the respective side edges 50 of the base sheet 48 are not bonded to, i.e., free from a part of the first elastic members 21a, the second elastic members 22a and the inner sheet 4. In regions extending outward from the regions 52, 56, 57, i.e. in regions spaced from the regions 56, 57 by the dimensions s and t, respectively, the outer sheet 5 is bonded to the first elastic members 21a, the leg-surrounding elastic members 19a and the inner sheet 4 by means of the hot melt adhesive 51 intermittently in the back-and-forth direction Y.

Figure 6:
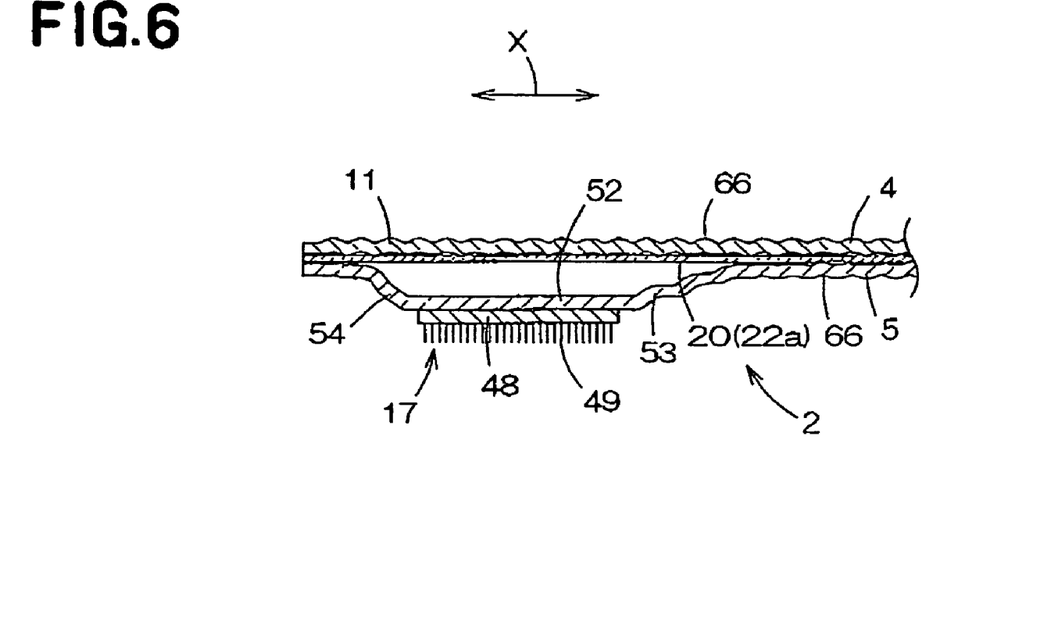
FIG. 6 is a view similar to FIG. 4, wherein elastic members are in contracted state.
Figure 7:
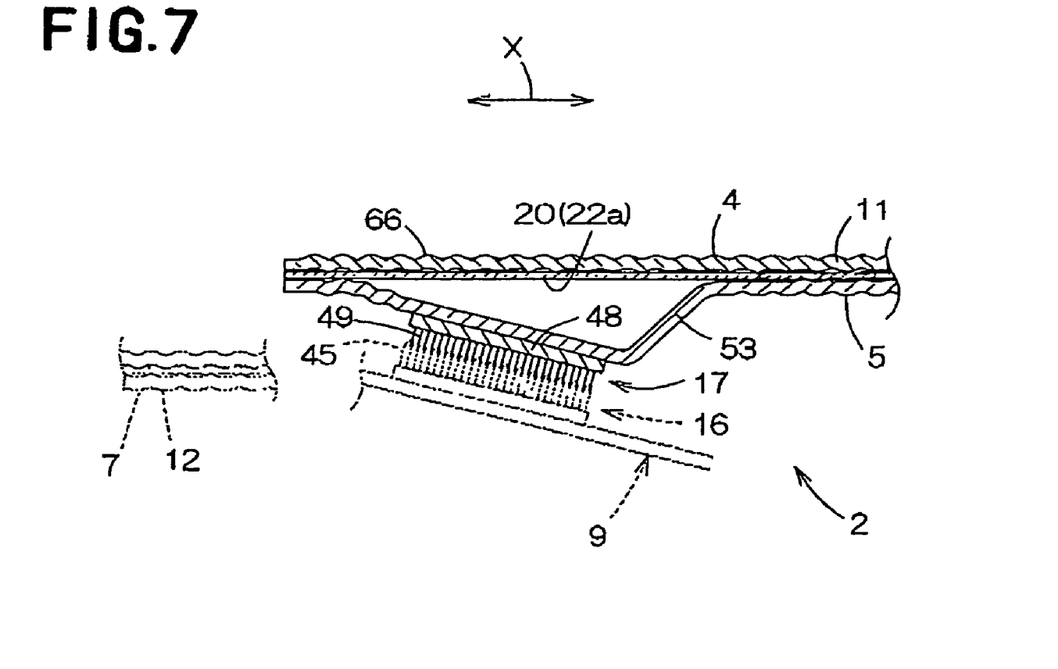
FIG. 7 is a view similar to FIG. 6, wherein transversely opposite side edge portions are connected together.

FIG. 6 is a view similar to FIG. 4 showing a side edge portion 11 when an elastic member 20 is in a contracted state and FIG. 7 is a view similar to FIG. 4 showing the side edge portion 11 when a side edge portion 12 is connected to the side edge portion 11 through the flap 9.

When the elastic members 20 contract in the body cover 2, the inner and outer sheets 4, 5 attached to the elastic members 20 contract in the width direction X and a plurality of fine gathers 66 undulating in the waist-surrounding direction appear in the inner and outer sheet 4, 5. However, in the side edge portions 11 of the front waist region 6 the regions 52, 53, 54 of the outer sheet 5 which are attached neither to the inner sheet 4 nor to the second elastic member 22a part from the inner sheet 4 so as to buldge outwardly of the diaper 1 (See FIG. 4). At this stage the base sheet 48 of the hook 17 maintains its flat state, even if the stiffness of the base sheet 48 is not so high, because the base sheet 48 is attached to the outer sheet 5 and the outer sheet 5 is attached neither to the inner sheet 4 nor to the second elastic members 20. The regions 53, 54 of the outer sheet 5 slant as depicted by the drawing and may make gathers in some cases. The hook part 17 in this condition all of the hooks 49 stand elect outwardly of the diaper 1 on the base sheet 48 and so easily engage with the loops 45 of the loop part 16 as depicted by FIG. 7.

In the diaper 1 constructed in this manner, even if the base sheet 48 of the hook part 17 is rather flexible in such an extent that the stiffness of the base sheet 48 is slightly higher than that of the outer sheet 5, the base sheet 48 is substantially not affected by contraction of the elastic members 20 and still in a flat state. It is thus ensured that all of the hooks 49 constituting the hook part 17 can be easily engaged with the loop part 16 and these part 16, 17 having been once engaged with each other are not easily disengaged from each other. Of the body cover 2, the inner and outer sheets 4, 5 may be formed from a material selected from the group including a nonwoven fabric, a plastic film and a woven fabric. At least one of the two sheets 4, 5 may be formed from a liquid-impervious sheet to improve a leak-barrier property of the diaper 1. The flap 9 also may be formed from a material or a combination of materials selected from the group including a nonwoven fabric, a plastic film and a woven fabric. It is also possible to use a sheet which is elastically stretchable in the width direction x as the material for the flap 9. While FIG. 2 illustrates the elastic members 20 as being arranged in the same layout in the front and rear waist regions 6, 7, the layout of the elastic members 20 may be appropriately varied in each of these two waist regions 6, 7. It is also possible to eliminate the elastic members 20 partially or entirely in the rear waist region 7 without departing from the scope of the invention. While the illustrated diaper 1 comprises the body cover 2 and the body fluid absorbent panel 3 provided separately of the body cover 2, the core 34 of the body fluid absorbent panel 3 may be sandwiched between the liquid-pervious inner sheet 4 and the liquid-impervious outer sheet 5 so that these components 2, 3, 34 may be coined into an integral structure.

Figure 8:
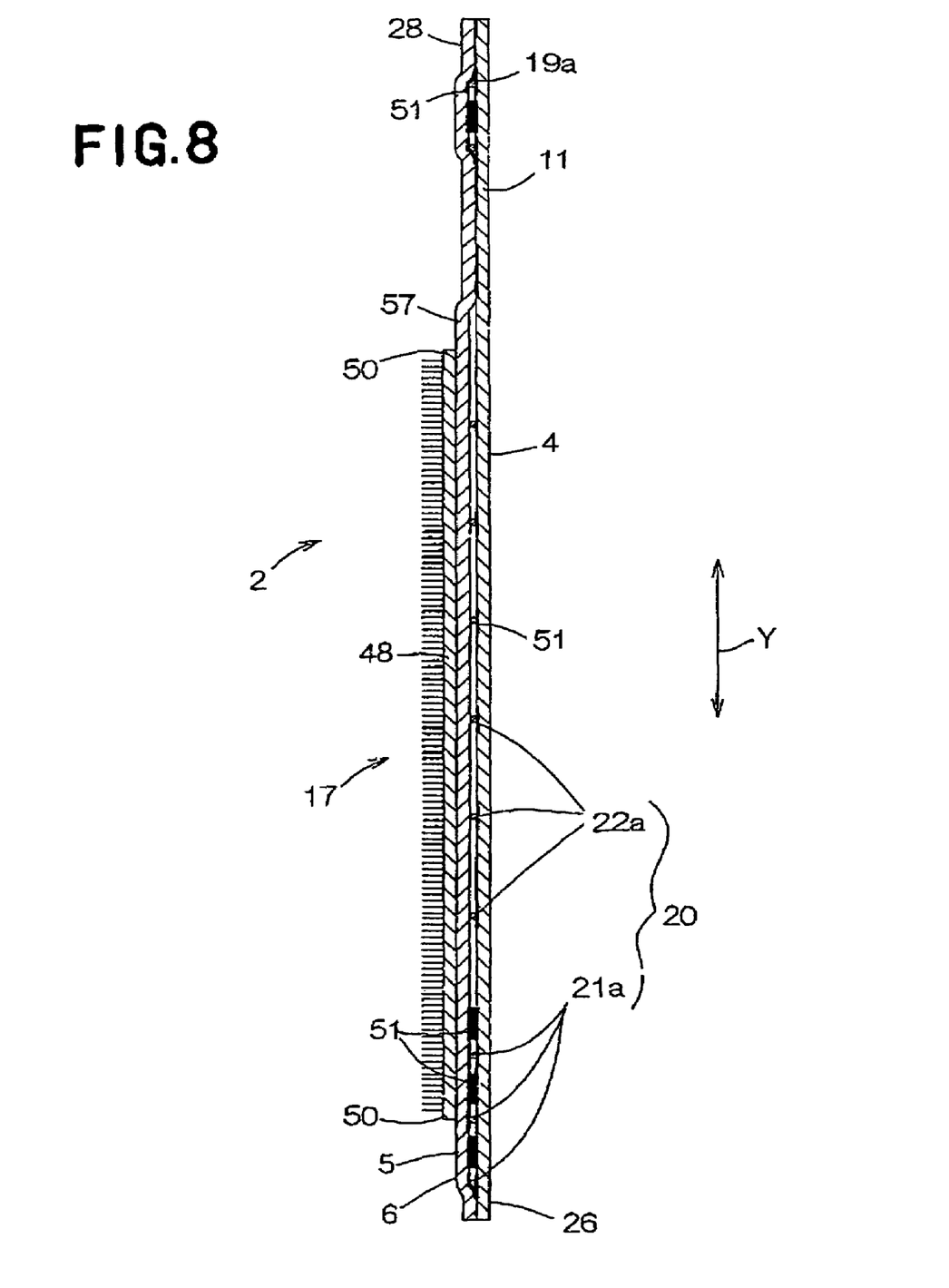
FIG. 8 is a view similar to FIG. 5, showing one preferred embodiment of the invention.

FIG. 8 is a view similar to FIG. 5, showing one preferred embodiment of the invention. According to this embodiment, the outer sheet 5 is bonded to three first elastic members 21a for the front waist region 6 and the inner sheet 4 by means of a hot melt adhesive 51 in the front end portion 26 in each of the side edge portions 11 and the base sheet 48 of the hook part 17 is bonded along its respective side edges 50 to the outer sheet 5. Of the outer sheet 5, a major part of the region 52 placed upon the base sheet 48 and the region 57 extending downward (upward as viewed in FIG. 8) from one of the side edges 50 of the base sheet 48 are bonded neither to the second elastic members 22a nor to the inner sheet 4. With such a unique arrangement of the hook part 17 on the body cover 2, the contraction of the elastic members 20 may result in the formation of gathers along the front end portion 26 but the major portion of the hook part 17 located aside from the front end portion 26 toward the crotch region 8 is free from the formation of the gathers. The object of the invention can be achieved also by the diaper 1 having the side edge portions 11 arranged in such a manner.

Figure 9:
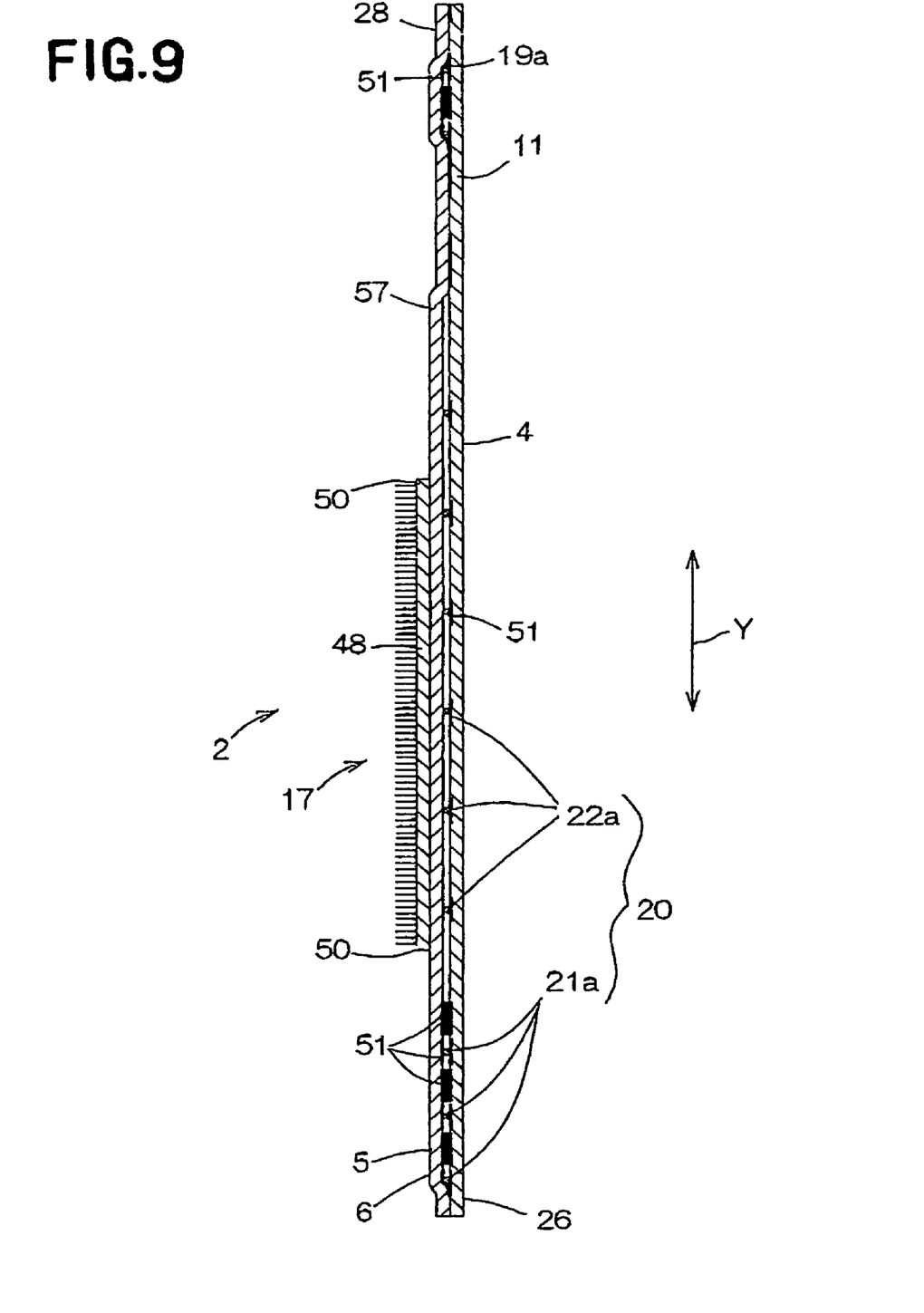
FIG. 9 is a view similar to FIG. 5, showing another preferred embodiment of the invention.

FIG. 9 is a view similar to FIG. 8, showing another preferred embodiment of the invention. The side edge portions 11 in this embodiment comprises the inner sheet 4, the outer sheet 5 and the elastic members 20 formed in the manner similar to the case depicted in FIG. 8. However, the base sheet 48 constituting the hook part 17 has a length shorter than the base sheet 48 of FIG. 8 as measured in the back-and-forth direction Y. Specifically, the base sheet 48 according to this embodiment does not extend to the front end portion 26 and therefore does not cross three first elastic members 21a. In addition, the hook part 17 crosses only a part of the plural second elastic members 22a. With such a hook part 17 also, gathers may not be formed even if the elastic members 20 contract.

Figure 10:
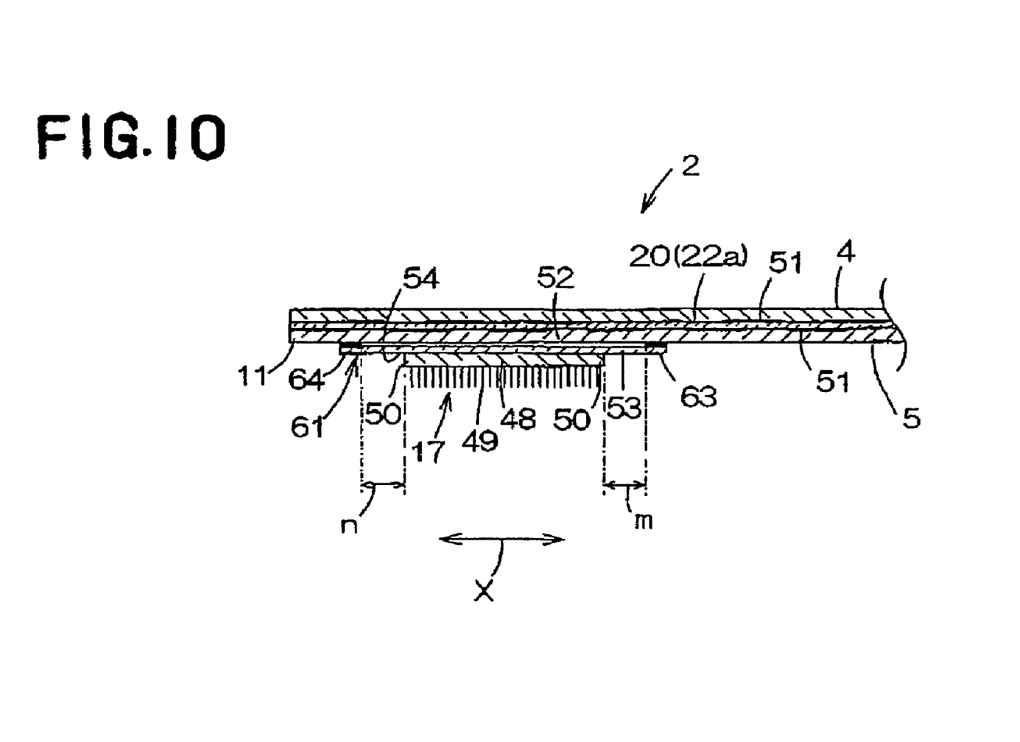
FIG. 10 is a view similar to FIG. 4, showing still another preferred embodiment of the invention.

FIG. 10 is a view similar to FIG. 4, showing another preferred embodiment of the invention. Each of the side edge portions 11 in this embodiment comprises the inner sheet 4, the outer sheet 5 and the elastic members 20 intermittently bonded together by means of the hot melt adhesive 51. The base sheet 48 constituting the hook part 17 is provided separately of the inner and outer sheets 4, 5 and attached by means of bonding or welding to a supporting sheet member 61 having a size larger than the base sheet 48 and a stiffness lower than that of the base sheet 48, preferably, a substantially the same stiffness as that of the outer sheet 5. The sheet member 61 extends outward beyond the respective peripheral side edges 50 of the base sheet 48 in the width direction X to define peripheral regions 53, 54 having desired width dimensions m, n and further extends outward beyond the peripheral regions 53, 54 to define regions 63, 64 along which the sheet member 61 is attached to the outer sheet 5. Such a sheet member 61 is indirectly attached to the elastic members 20 and the inner sheet 4 through the outer sheet 5.

Figure 11:
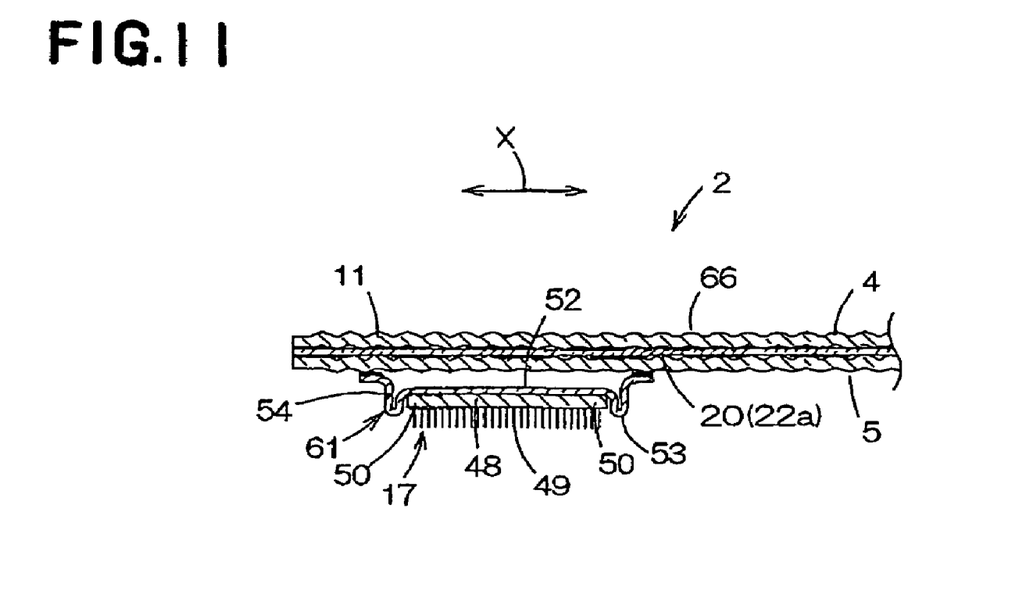
FIG. 11 is a view similar to FIG. 4, wherein elastic members are in contracted state.

FIG. 11 is a view similar to FIG. 10, wherein the elastic member 20 is in a contracted state. Of the elastic members 20 in the illustrated state, the second elastic members 22a intermittently attached to the inner and outer sheets 4, 5 contract in the width direction X and form these inner and outer sheets 4, 5 with a plurality of gathers 66. The region 52 of the sheet member 61 in which the sheet member 61 is attached to the base sheet 48 is maintained in a flat state together with the base sheet 48 and the peripheral regions 53, 54 are curved so as to be convex outward (downward as viewed in FIG. 11) in the vicinity of the peripheral regions 50. The peripheral regions 53, 54 curved in this manner serve to diminish a possibility that the side edges 50 of the base sheet 48 might irritate the wearer's skin. When the peripheral regions 53, 54 are relatively stiff, these peripheral regions 53, 54 may slant as illustrated in FIG. 6. As will be apparent from this embodiment, if the outer sheet 5 is bonded to the inner sheet 4 and the elastic members 20, it will be preferred to attach the base sheet 48 of the hook part 17 indirectly to the outer sheet 5 instead of directly attaching the base sheet 48 to the outer sheet 5. By attaching the hook part 17 to the sheet member 61 in this manner, the hook part 17 can be maintained free from the elastic members 20 as well as from the inner sheet 4.

Figure 12:
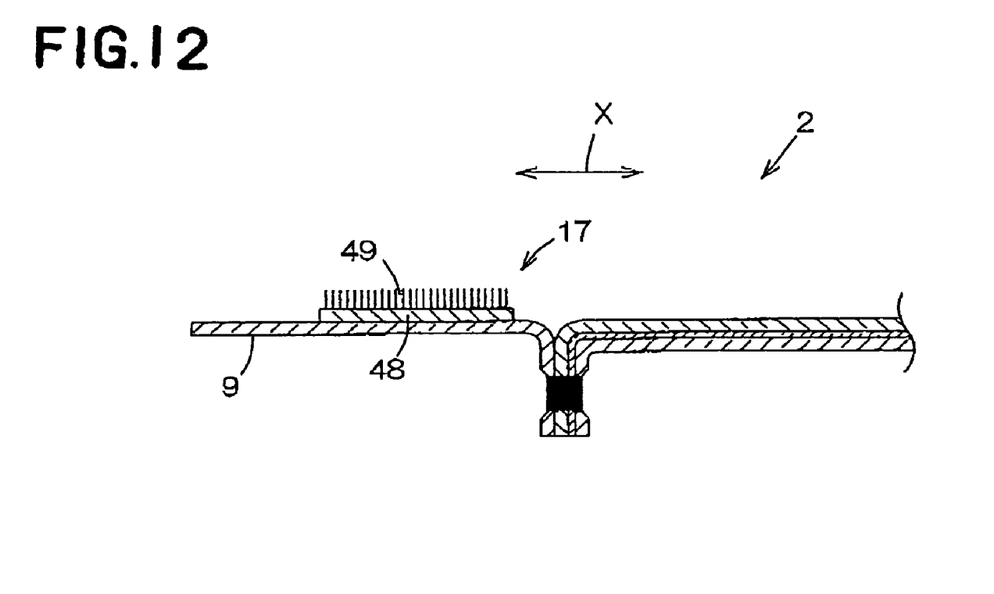
FIG. 12 is a view similar to FIG. 3, showing still another preferred embodiment of the invention.
Figure 13:
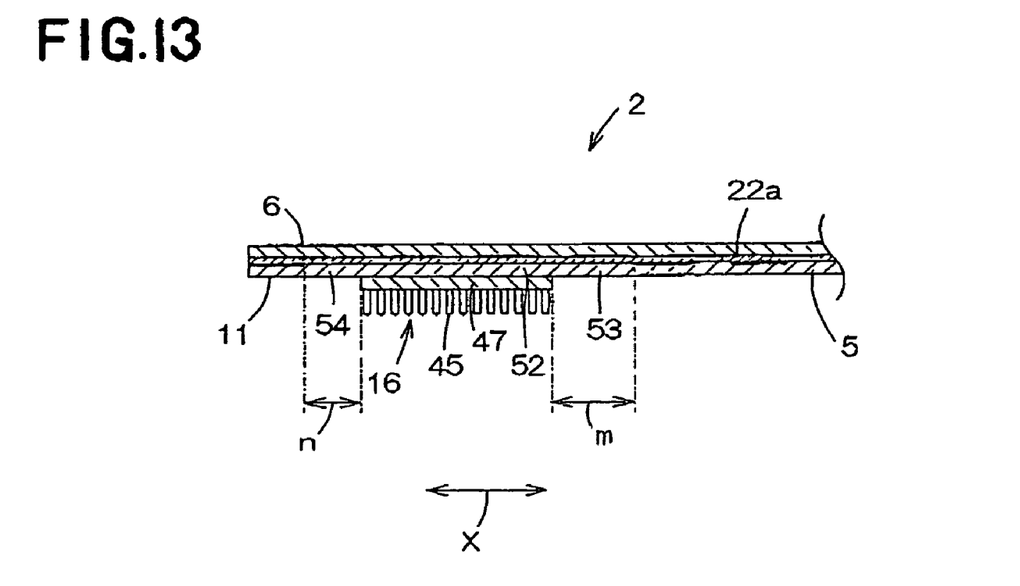
FIG. 13 is a view similar to FIG. 4, showing still another preferred embodiment of the invention.

FIGS. 12 and 13 are views similar to FIGS. 3 and 4, respectively, showing another preferred embodiment of the invention. In this embodiment the base sheet 48 which is a part of the hook part 17 is attached to the inner surface of the flap 9 and a plurality of the hooks 29 are formed on the inner surface of the base sheet 48. The base sheet 47 of the loop part 16 extending along the side edge portion 11 of the front waist region 6 of the body cover 2 crosses the second elastic members 22a. The base sheet 47 is attached to the outer surface of the outer sheet 5 and a plurality of the loops 45 are formed as fastening elements on the outer, surface of the base sheet 47. The region 52 and the peripheral regions 53, 54 of the outer sheet 5 are attached neither to the inner sheet 4 nor to the second elastic members 22a.

Figure 14:
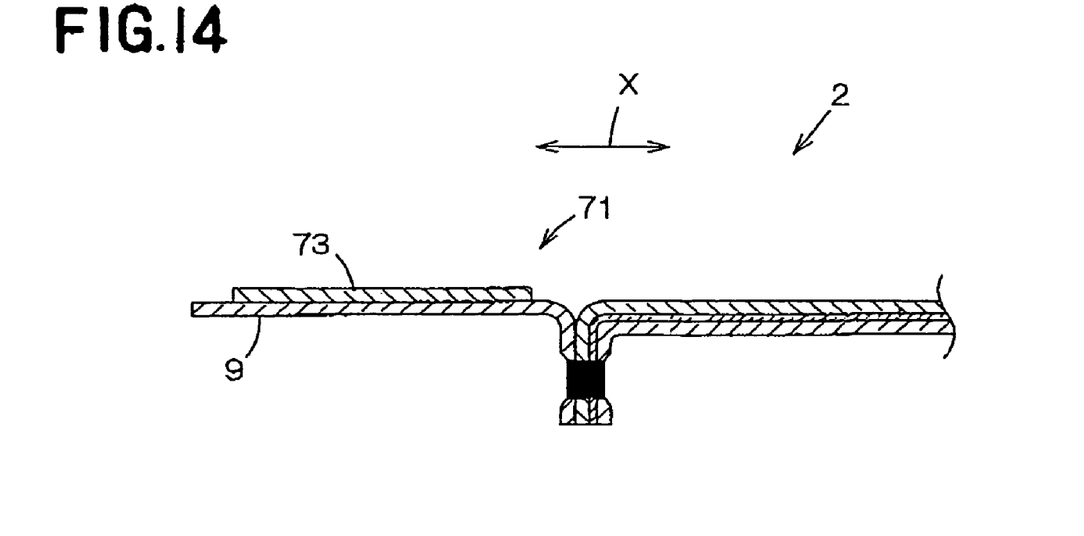
FIG. 14 is a view similar to FIG. 3, showing still another preferred embodiment of the invention.
Figure 15:
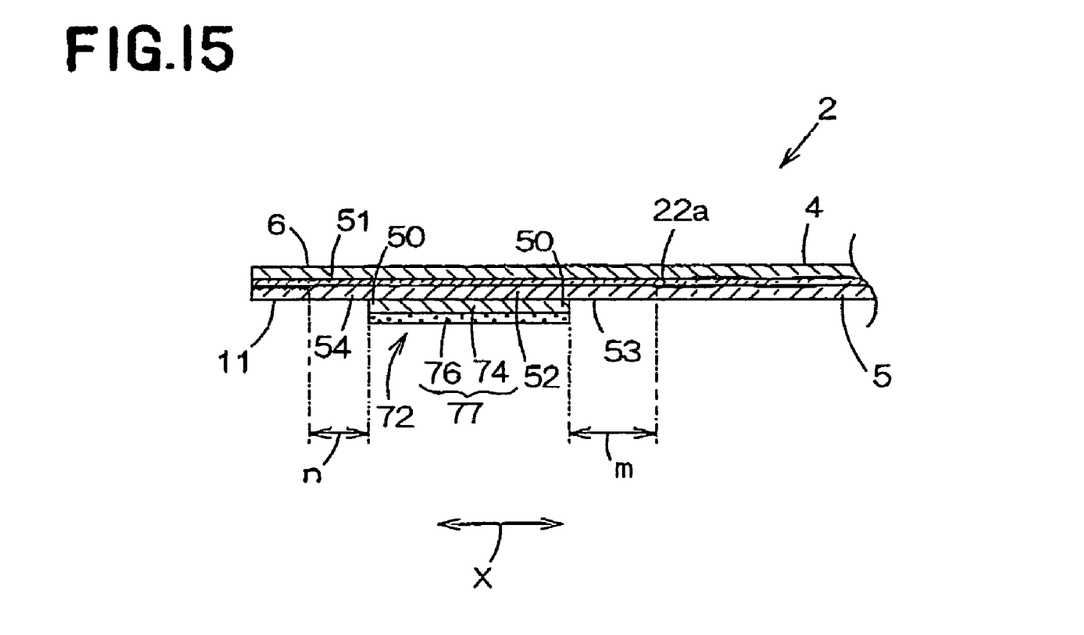
FIG. 15 is a view similar to FIG. 4, showing still another preferred embodiment of the invention.

FIGS. 14 and 15 are views similar to FIGS. 3 and 4, respectively, showing another preferred embodiment of the invention. In this embodiment the fastening means comprising the loop part 16 and the hook part 17 depicted in FIGS. 3 and 4 is replaced with a fastening means comprising a target area 71 and a sticky area 72 depicted in FIGS. 14 and 15. In FIG. 14 the flap 9 is made of a nonwoven fabric, and a plastic film 73 constituting the target area 71 is unseperably attached to the inner surface of the flap 9. In FIG. 15 the sticky area 72 is formed from a sticky sheet 77 comprising a base sheet 74 and an adhesive agent 76 coated therewith as a fastening element and the sticky sheet 77 is unseperably attached to the outer surface of the outer sheets. The sticky area 72 is extending along the side edge portion 11 of the front waist region 6 and crosses the second elastic members 22a. The sticky area 72 can be repeatedly attached to the inner surface of the sheet 73 of the target area 71. The outer sheet 5 is attached to the inner sheet 4 and the second elastic members 22a with a hot-melt adhesive 51 intermittently along the second elastic members 22a in the same manner as depicted in FIG. 4. However, the outer sheet 5 is attached neither to the inner sheet 4 nor to the second elastic members 22a in the region 52 attached to the base sheet 74 and the peripheral regions 53, 54 having widths m, n respectively from the peripheral side edges 50 of the base sheet 74. In the present invention it is possible to replace the target area 71 of FIG. 14 with the sticky area 72 and the sticky area 72 of FIG. 15 with the target area 71. If the target area 71 is provided in the front waist region 6, the surface of the sheet 73 of the target area 71 works as the fastening element of the fastening means.

Without departing from the scope of the invention, it is possible to shape the front waist region 6 so as to serve as the rear waist region and to shape the rear waist region 7 so as to serve as the front waist region. It is also possible to attach the loop part 16 to the outer surface of the flap 9 and to attach the hook part 17 to the inner surface of the body cover 2 without departing from the scope of the invention. In this alternative case, the inner sheet 4 to which the hook part 17 is attached is attached neither to the elastic members 20 nor to the outer sheet 5 in the vicinity of the hook part 17. In the present invention the rear waist region 7 may be extended from each side of the front waist region so as to be transversely larger than the front waist region 6 instead of providing the flaps 9 separately of the body cover 2. However, each extended portion of the rear waist region 7 does not have such a tendency to overlap with the front waist region 6 by itself as the flap 9 of FIG. 1 shows. The present invention is applicable, not only to the disposable diaper 1, to other articles such as a training pant, a diaper for incontinent patients, a pant for holding urine-absorbent pad and a diaper cover.

What is claimed is:

1. A disposable wearing article, comprising:
   a crotch region having a back-and-forth direction and a width direction orthogonal to each other;
   a first waist region and a second waist region respectively extending forward and rearward from said crotch region in said back-and-forth direction of said crotch region, said first and second waist regions respectively having end portions each extending in said width direction;

at least in said first waist region, a plurality of elastic members stretched in said width direction being interposed between a first sheet and a second sheet placed upon each other;

a fastener comprising a first fastening member and a second fastening member engageable with each other, said first waist region being formed with said first fastening member while said second waist region being formed with said second fastening member;

said first fastening member comprising a base sheet and a first fastening element formed on one of two opposite surfaces of said base sheet and extending across said elastic members in said back-and-forth direction;

the other surface of said base sheet being directly attached to an underlying section of the first sheet in said first waist region, wherein said first sheet has a stiffness lower than said base sheet, and the entire section of the first sheet underlying said base sheet is free of direct attachment to said second sheet and said elastic members.

2. The disposable wearing article as set forth by claim 1, wherein said first sheet further comprises lateral sections outwardly spaced in the back-and-forth direction and the width direction from peripheral edges of said base sheet by a given dimension, and directly attached to said second sheet and said elastic members.

3. The disposable wearing article as set forth by claim 1, wherein said first sheet defines one of (a) an inner sheet of said wearing article adapted to face, in use, a wearer, and (b) an outer sheet of said wearing article adapted to face, in use, away from the wearer.

4. The disposable wearing article as set forth by claim 1, wherein
said fastener is a mechanical fastener comprising a hook part and a loop part;
said first fastening member is one of the hook part and the loop part of said mechanical fastener, said first fastening element comprising either hooks of said hook part or loops of said loop part, respectively; and
said second fastening member is the other one of said hook and loop parts of the mechanical fastener.

5. A disposable wearing article having a longitudinal direction and a transverse direction orthogonal to each other, said article comprising:
first and second sheets placed upon each other to define a first waist region, a second waist region, and a crotch region extending in the longitudinal direction between said first and second waist regions;
a plurality of elastic members extending in the transverse direction at least in the first waist region, being disposed between said first and second sheets, and being contractibly attached to at least one of said first and second sheets; and
a fastener comprising matching first and second fastening members disposed in said first and second waist regions, respectively;
wherein
said first fastening member comprises a base sheet and a first fastening element;
said first fastening element is engageable with a matching second fastening element of the second fastening member and is disposed in a middle region of said base sheet;
the middle region of said base sheet overlies said elastic members, is not directly attached to underlying sections of said elastic members, and is separated from the underlying sections of said elastic members as the elastic members contract.

6. The disposable wearing article as set forth by claim 5, wherein
said first fastening member is one of (a) a sticky sheet coated with an adhesive agent and (b) a sheet constituting a target zone releasably attachable to said sticky sheet, said first fastening element being one of (a) said adhesive agent and (b) a surface of said sheet constituting said target zone, respectively; and
said second fastening member is the other one of said sticky sheet and said sheet.

7. The article of claim 5, wherein said base sheet is directly attached to said first sheet in a zone where said first sheet is not directly attached to the underlying sections of said elastic members;
the first sheet in said zone is separated from the underlying sections of said elastic members as the elastic members contract.

8. The article of claim 5, further comprising a sheet member to which said base sheet is directly attached and which comprises
lateral regions that extend outwardly beyond a periphery of said base sheet and are directly attached to said first sheet; and
a central region which is located between said lateral regions, corresponds to the middle region of said base sheet, and is free of direct attachment to said first sheet;
wherein the central region of said sheet member is separated from the first sheet as the elastic members contract.

9. The disposable wearing article as set forth by claim 1, wherein the first fastening member and the second fastening member are directly engageable with each other in use to connect the first waist region and the second waist region, thereby defining a waist hole and a pair of leg holes.

10. The disposable wearing article as set forth by claim 9, wherein, when the first fastening member and the second fastening member are directly engageable with each other in use to connect the first waist region and the second waist region, the second sheet defines an inner surface of the article and is adapted to face a wearer.

11. The disposable wearing article as set forth by claim 10, wherein the elastic members include segments which are directly sandwiched between the underlying section of the first sheet and a corresponding section of the second sheet, are contactable with the underlying section of the first sheet, and are free of direct attachment to said underlying section of the first sheet.

12. The disposable wearing article as set forth by claim 11, wherein
a portion of the base sheet, to which the underlying section of the first sheet is directly attached, is sandwiched between the first fastening element and the underlying section of the first sheet.

13. The disposable wearing article as set forth by claim 1, wherein the elastic members include segments which are directly sandwiched between the underlying section of the first sheet and a corresponding section of the second sheet, are contactable with the underlying section of the first sheet, and are free of direct attachment to said underlying section of the first sheet.

14. The disposable wearing article as set forth by claim 1, wherein
a portion of the base sheet, to which the underlying section of the first sheet is directly attached, is always sandwiched between the first fastening element and the underlying section of the first sheet.

* * * * *